US00PP13442P2

(12) United States Plant Patent
Tristram

(10) Patent No.: US PP13,442 P2
(45) Date of Patent: Dec. 31, 2002

(54) SCABIOSA PLANT NAMED 'WALMINIPINK'

(76) Inventor: David Ralph Tristram, Old Rectory Arundel, Binsted, W. Sussex, BN18 0LL (GB)

( * ) Notice: Subject to any disclaimer, the term of this patent is extended or adjusted under 35 U.S.C. 154(b) by 0 days.

(21) Appl. No.: 09/962,381

(22) Filed: Sep. 25, 2001

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Mark P. Bourgeois

(57) ABSTRACT

A new cultivar of *Scabiosa columbaria* named 'Walminipink' that is characterized by its small plant size, compact plant habit, proportionately sized pink flowers, prolific and continuous flowering, and sterility.

1 Drawing Sheet

CROSS-REFERENCE TO RELATED APPLICATIONS

The present application is co-pending with another application entitled Scabiosa Plant Named 'Walminiblue' (Application Ser. No. 09/962,382).

LATIN NAME OF THE GENUS AND SPECIES

*Scabiosa columbaria.*

VARIETY DENOMINATION

'Walminipink'.

BACKGROUND OF THE INVENTION

The present invention relates to a new and distinct cultivar of Scabiosa plant, botanically known as *Scabiosa columbaria* and will be referred to hereafter by its cultivar name 'Walminipink'. *Scabiosa columbaria* is a hardy perennial grown for landscape use.

The new Cultivar, 'Walminipink', was discovered in 1990 by the inventor at his nursery in West Sussex, England. 'Walminipink' was discovered as a naturally occurring mutation, amongst a large crop of *Scabiosa columbaria* 'Pink Mist' (U.S. Plant Pat. No. 8,957). The new invention was discovered as a whole plant, however it originated as a single cutting taken from 'Pink Mist'. Several selections were discovered and observed before 'Walminipink' was selected as unique and desirable for its characteristics of plant size, plant habit, flower color, and sterility.

The new variety of Scabiosa can be characterized by its smaller size: the foliage dimensions, diameter of the flower heads and the height of the plant are less in comparison to the parent plant, 'Pink Mist'. The new invention has never set fruit and all flowers observed have been self-sterile. Near self-sterility is a characteristic of 'Pink Mist' and the inventor's variety 'Butterfly Blue' (un-patented) but is not a characteristic of any other commercial cultivars of *Scabiosa columbaria* known to the inventor. The flowers of *Scabiosa columbaria* are typically blue lavender and therefore, the new invention and 'Pink Mist' are unique in having flowers with distinctly pink and sterile flowers. The new cultivar is similar to both 'Butterfly Blue' and 'Pink Mist' in that it has a compact habit and has a continuous and prolific flowering habit.

Asexual reproduction of the new cultivar was first accomplished by taking cuttings in West Sussex, England by the inventor in 1990. The characteristics of this cultivar have been determined to be stable and are reproduced true to type in successive generations both by vegetative cuttings and by tissue culture.

SUMMARY OF THE INVENTION

The following traits have been repeatedly observed and are determined to be the basic characteristics of the new cultivar. These attributes in combination distinguish the new invention from wild forms of *Scabiosa columbaria* and distinguish it as a new and distinct cultivar. 'Walminipink' has not been tested under all possible conditions and phenotypic differences may be observed with variations in environmental, climatic, and cultural conditions:

1. 'Walminipink' is smaller in height and has less of a spread in comparison to 'Pink Mist'. 'Walminipink' attains 10 to 18 cm in height and 10 to 20 cm in width while 'Pink Mist' attains 15 to 30 cm in height and 17 to 30 cm in width, dependent on growing conditions.

2. The plant habit of 'Walminipink' is compact with a tight rosette of basal growth.

3. The flowers of 'Walminipink' are smaller than those of 'Pink Mist', ranging from 2.5 to 4.3 cm in diameter while the flower size of 'Pink Mist' ranges from 4.0 to 6.0 cm in diameter. This range in flower size is found on a single plant.

4. The flowers of 'Walminipink' are pink and are similar in color to that of 'Pink Mist' but unique in comparison to all other cultivars known to the inventor.

5. 'Walminipink' blooms continuously and profusely from early spring until frost. Typically, there are 10–12 flower heads showing color at one time.

6. The flowers of 'Walminipink' are presumed to be self-sterile as fruit set has not been observed to date.

BRIEF DESCRIPTION OF THE DRAWING

The photograph of 'Walminipink' is of a 6 month-old plant in a six-inch container. The plant was grown in a cold frame in Walberton, Sussex, England, under natural lighting and with an average daytime temperature of 7° C. and an average nighttime temperature of 30° C. The colors in these photographs are as accurate as possible by conventional photography.

BOTANICAL DESCRIPTION OF THE PLANT

The following is a detailed botanical description of the new cultivar as grown under greenhouse conditions in Encinitas, Calif. The 6 month old plant was grown under natural lighting with an average daytime temperature of 75° F. and an average nighttime temperature of 70° F. and a constant feed of 20-10-20 fertilizer at a rate of 175 ppm Nitrogen. General plant descriptions describe a plant as observed in the inventor's nursery in West Sussex, England for 4 years. The color determination is in accordance with The R.H.S. Colour Chart of The Royal Horticultural Society, London, England, except where general color terms of ordinary dictionary significance are used.

Botanical classification: *Scabiosa columbaria* 'Walminipink'.

Market classification: Hardy perennial for landscape use.

Parentage: Naturally occuring mutation of *Scabiosa columbaria* 'Pink Mist' (U.S. Plant Pat. No. 8,957).

Plant description:

*Blooming period.*—Natural flowering season is from early spring until frost in the Northern hemisphere.

*Plant habit.*—Dense, mounded rosetted with upright flowering stems.

*Height and spread.*—10 to 18 cm in height in bloom (bloom stalks vary in height) and 10 to 20 cm in spread depending on growing conditions.

*Hardiness.*—Zone 3–9.

*Type.*—Hardy herbaceous perennial.

*Propagation.*—By terminal tip cuttings and division.

*Root system.*—Fibrous, branching.

*Time to initiate roots.*—10 to 15 days in the summer months at temperatures of 64° F. to 72° F. and 15 to 20 days in the winter months at temperatures of 53° F. to 60° F.

*Vigor.*—A rooted cutting will establish roots and initiate flowers in a six-inch container after 15 weeks at an average temperature of 75° F. and constant fertilizer feed of 20-10-20 at a rate of 175 ppm Nitrogen.

*Culture.*—Well drained soils of average fertility in full sun.

*Diseases and pests.*—Powdery mildew is the only known disease known to be a problem in the garden.

Foliage description (characteristics that differ in basal and flowering stem leaves):

*Basal leaves.*—Simple, opposite arrangement, obovate to oblanceolate, entire to coarsely lobed with lobes and apex rounded or slightly acute, 4.0 to 10 cm in length and 1.5 to 2.5 cm in width.

*Flowering stem leaves.*—Simple, obovate, pinnatifid to pinnatisect with up to 7 ovate to linear pinnae on each side, leaflets are opposite or alternately arranged, with apices of leaf and leaflets acute. Stem leaves are 4.0 to 10.0 cm in length and 2.0 to 4.0 cm in width.

Foliage description (characteristics that are similar for the basal and flowering stem leaves):

*Venation.*—Not prominent, with the exception of the mid-rib on the lower portion of the leaves, color 139D (upper and lower surface).

*Surface.*—Pubescent on upper and lower surfaces and veins.

*Color.*—Upper surface, mature and immature leaves, 137A. Lower surface, mature and immature leaves, 137C.

Flowering stem description (peduncle):

*Shape.*—Round.

*Size.*—1.5–3.0 mm in diameter in width, 10 to 18 cm in height with the longer stems occurring when temperatures are warmer, above 75° F.

*Surface.*—Pubescent.

*Color.*—138B.

*Branching.*—Initially none, but as the flower stem elongates, lateral branches are produced, each with a single flower head.

Flower description:

*Type.*—Terminal flat heads, regular to slightly irregular, round, numerous with outer florets that are larger than the inner florets.

*Fragrance.*—None.

*Size.*—2.5 to 4.3 cm in diameter, approximately 1.0 cm in depth.

*Lastingness of the flower heads.*—Approximately one week in summer and up to two weeks in colder periods, not self cleaning; bristled calyx and involucral bracts are persistent.

*Buds.*—Dome-shaped, emerge 143D and 5 mm in diameter, gradually changing to the petal color 76A, with a diameter of 1.0 to 1.5 cm.

*Involucral bracts.*—10–15 in a single row, held horizontally, linear-lanceolate, apex acute, length ranges from 5.0 to 10.0 mm, 1.5 to 3.0 mm in width, base of bract is 145A, portion of bract extended beyond calyces is 137A, pubescent.

*Calyx.*—Densely packed to form a receptacle-like structure. Cupular, composed of 5 united sepals, 144 C, 1.5 mm in width and 2.0 mm in height with a bristle, 202A, extending 2.0 mm in length beyond each sepal. Entire Calyx is persistent.

*Corolla.*—Zygomorphic, 5 petals, partially united near base. Outer florets are 8 to 15 mm in length and 10 to 15 mm in width, approximately 15–30 ray florets per inflorescence, color varies from 76A to 77D on both surfaces depending on night temperatures, with cooler nights resulting in petals that are more pink in color (77D). Inner florets are 4–7 mm in length and 3–4 mm in width, approximately 40–100 disc florets per inflorescence, color 76A fading to 159D at maturity.

Reproductive organs: Stamens; 4, partially fused, can be included or exserted; if exserted, they extend 2–4 mm above corolla in early stages of flowering and then are not visible, 68D to 77D in color (paler in lower light levels), no pollen was observed to date. Pistil; 1, 159D, clearly visible in later stage of flowering, extending up to 6.0 mm beyond corolla, ovary is superior and non-visible.

Fruit/seed: Fruit production has not been observed to date, presumed to be sterile.

I claim:

1. A new and distinct cultivar of Scabiosa Plant named 'Walminipink' as described and illustrated.

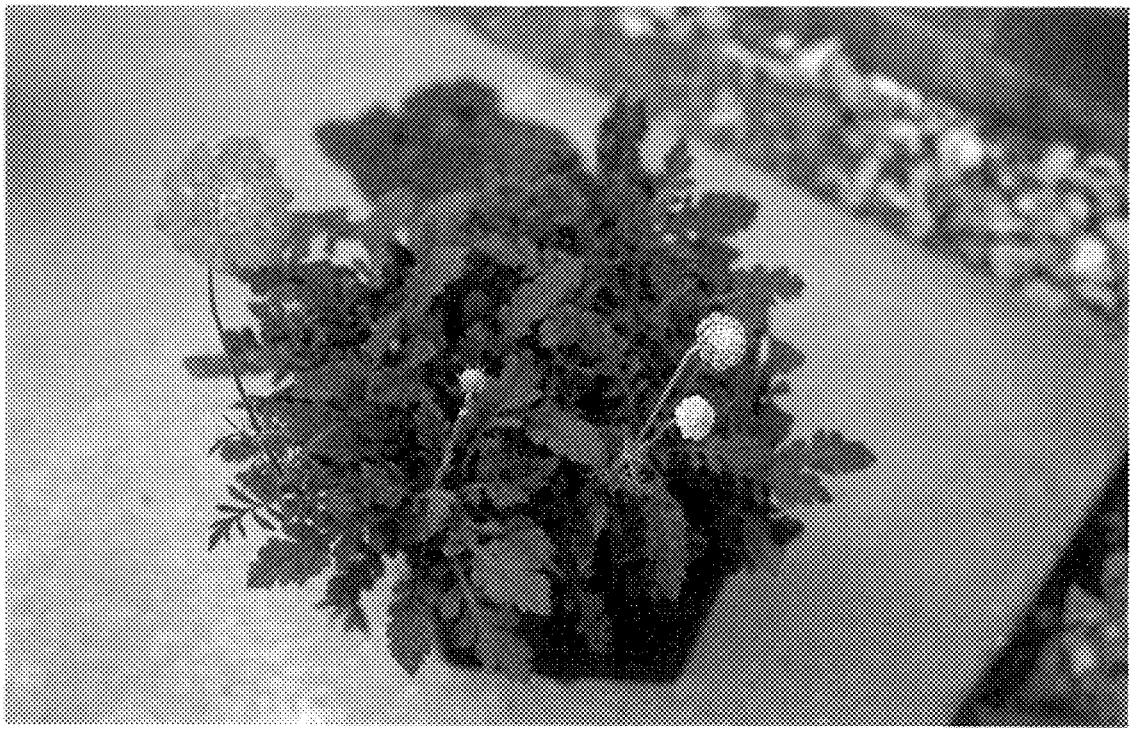

* * * * *